United States Patent [19]
Lin

[11] Patent Number: 5,702,481
[45] Date of Patent: Dec. 30, 1997

[54] BONE MARROW CAVITY FIXATION DEVICE FOR TREATING A FRACTURED BONE

[76] Inventor: Chih-I Lin, 14292 Spring Vista La., Chino Hills, Calif. 91709

[21] Appl. No.: 442,111

[22] Filed: May 16, 1995

[51] Int. Cl.$^6$ ..................................... A61F 2/36
[52] U.S. Cl. .................. 623/23; 623/18; 606/63
[58] Field of Search .................. 606/53, 60, 62, 606/63, 64, 68, 72, 73, 95; 623/16, 22, 23

[56] References Cited

U.S. PATENT DOCUMENTS

| | | | |
|---|---|---|---|
| 3,939,497 | 2/1976 | Heimke et al. | 3/1.912 |
| 4,237,875 | 12/1980 | Termanini | 128/92 |
| 4,520,511 | 6/1985 | Gianezio et al. | 3/1.193 |
| 4,911,722 | 3/1990 | Crespy | 623/23 |

FOREIGN PATENT DOCUMENTS 2733826  5/1980  Germany .

OTHER PUBLICATIONS

Catalog of the P.C.A.; E–Series and E–Series Textured Hip Systems; by Howmedica Corporation.
Catalog of the P.C.A.; Total Hip System; by Howmedica Corporation.

*Primary Examiner*—Michael Buiz
*Assistant Examiner*—David O. Reip
*Attorney, Agent, or Firm*—Bacon & Thomas

[57] ABSTRACT

A bone marrow cavity fixation device for treating a fractured bone is composed of a tubular body, a plurality of diameter-adjusting elements, an adjustment element, and an urging element. The tubular body is provided axially with a hollow interior and is further provided peripherally with a plurality of through holes communicating the hollow interior with the outside of the tubular body. The diameter-adjusting elements are disposed movably in the through holes such that the diameter-adjusting elements can be so urged by the adjustment element located in the hollow interior as to jut out of the through holes to bring about an increase in diameter of the tubular body. The adjustment element can be actuated by a rotational motion of the urging element which is located in the hollow interior such that the top end of the adjustment element is urged by the lower end of the urging element. The diameter-adjusting elements are provided respectively with a retaining element engageable securely with the retaining device of the tubular body or the adjustment element.

4 Claims, 4 Drawing Sheets

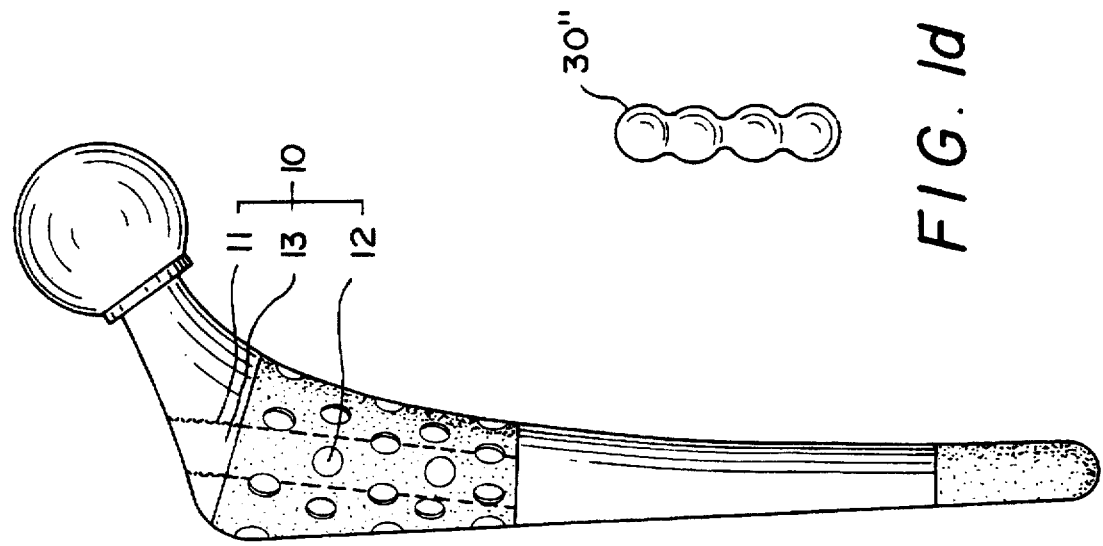
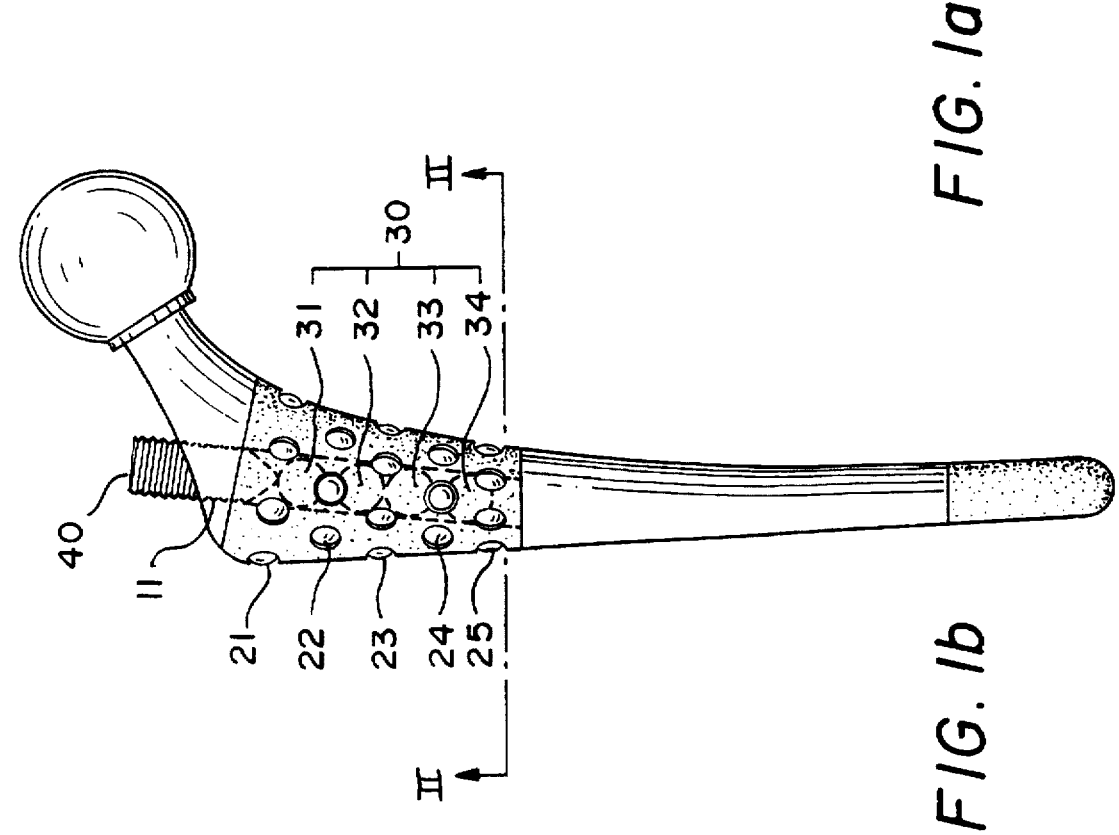

BONE MARROW CAVITY FIXATION DEVICE FOR TREATING A FRACTURED BONE

FIELD OF THE INVENTION

The present invention relates generally to a bone fixation device, and more particularly to a bone marrow cavity fixation device for the surgical treatment of a fractured bone.

BACKGROUND OF THE INVENTION

The Howmedica Corporation of the United States disclosed P.C.A.® E-series artificial hip joints, which are solid in construction and have an outer diameter that can not be adjusted. Such conventional hip joints as described above have a relatively poor fixing effect in view of the fact that the E-Series artificial hip joints are incapable of giving an instant fixation effect to a femur which is intended to be fixed, and that the contact area between the bone marrow cavity and the E-Series artificial hip joints is rather limited.

SUMMARY OF THE INVENTION

It is therefore the primary objective of the present invention to provide a bone marrow cavity fixation device with means capable of giving an intensive support to the bone marrow cavity and of giving an instant fixation effect.

It is another objective of the present invention to provide a bone marrow cavity fixation device capable of making contact with a greater area of the bone marrow cavity so as to bring about an instant fixation effect.

In keeping with the principle of the present invention, the foregoing objectives of the present invention are attained by a bone marrow cavity fixation device comprising a tubular body, a plurality of diameter-adjusting elements, an adjustment element, and an urging element.

The tubular body is provided at the top end thereof with an opening and is further provided peripherally with a plurality of through holes communicating the hollow interior of the tubular body with the outside of the tubular body.

The diameter-adjusting elements are received in the through holes of the tubular body such that the diameter-adjusting elements can be caused to jut out so as to adjust the diameter of the tubular body. The diameter-adjusting elements are provided respectively with a holding element.

The adjustment element is disposed in the hollow interior of the tubular body such that the adjustment element is in contact with the inner end of each of the diameter-adjusting elements.

The urging element is inserted into the hollow interior of the tubular body via the open top of the tubular body such that the top end of the adjustment element is urged by the lower end of the urging element. As the urging element is rotated to actuate the adjustment element, the diameter-adjusting elements are forced to jut out so that the outer diameter of the tubular body is therefore increased.

The tubular body or the adjustment element is provided with a retaining means engageable with the holding elements of the diameter-adjusting elements so as to ensure that the diameter-adjusting elements are always engaged securely with the tubular body or the adjustment element.

The tubular body is not limited in shape. For instance, the tubular body may be similar in shape to a marrow screw or an artificial hip joint of the prior art when the tubular body of the present invention is used in place of the marrow screw or the artificial hip joint of the prior art. The tubular body is provided axially with a hollow interior and is further provided peripherally with a plurality of through holes communicating the hollow interior with the outside of the tubular body.

The tubular body is divided into three to ten, preferably three to six, peripheral areas, each of which has two to ten, preferably two to six, through holes. The through holes located in the same peripheral area are preferably located on the same cross-sectional area. The angles formed by two adjacent through holes are preferably and substantially equal to one another. The peripheral areas are preferably provide with the through holes which are corresponding in number to one another and are arranged alternately or correspondingly on the straight lines parallel to the axis of the tubular body.

The diameter-adjusting elements are shaped and dimensioned to cooperate with the through holes of the tubular body. It is suggested that the diameter-adjusting elements are cylindrical in shape and are provided respectively at the outer end thereof with an arcuate surface of a considerable curvature. In addition, the diameter-adjusting elements are provided respectively with a holding element engageable with the retaining means of the tubular body or the adjustment element. If the holding element of the diameter-adjusting element is intended to engage the retaining means of the tubular body, the holding element of the diameter-adjusting element is preferably located in the vicinity of the outer end of the diameter-adjusting element. On the other hand, if the holding element of the diameter-adjusting element is intended to engage the retaining means of the adjustment element, the holding element of the diameter-adjusting element is preferably located in the proximity of the inner end of the diameter-adjusting element. The holding element of the diameter-adjusting element and the retaining means of the tubular body or the adjustment element are similar in construction to any retaining means of the prior art.

The adjustment element is changeable diametrically as it is advanced gradually in the tubular body or withdrawn gradually from the tubular body. The adjustment element may be a corrugated shaft or eccentric bearing. The corrugated shaft may be made up of a plurality of spherical or oblong bodies which may be formed integrally. The eccentric bearing comprises an eccentric circular track or oblong track. On the basis of the structural simplicity, the corrugated shaft is generally preferred to the eccentric bearing and is preferably composed of a plurality of spherical bodies forming a corrugated shaft.

When the corrugated shaft is used as the adjustment element, the retaining means is preferably located in the vicinity of the outer end of the through holes of the tubular body. The retaining means may be a retaining hole having a diameter smaller than that of the holding element of the diameter-adjusting elements. The retaining hole may be formed by making the outer end of the through hole smaller in diameter. It is also suggested that the tubular body may be provided with a casing having a plurality of retaining holes.

According to the present invention, the eccentric bearing is used preferably as the adjustment element while the retaining means is located on the adjustment element. For example, the outer holes of the eccentric circular track or oblong track of the eccentric bearing are used as retaining holes. The holding element of the diameter-adjusting element may be a protuberance having a diameter greater than that of the retaining holes.

The protuberance of the holding element of the diameter-adjusting element may be an elastic body capable of springing back to its original size and shape after being pressed and released.

The urging element is inserted into the tubular body via the open top of the tubular body such that the position of the adjustment element is adjusted by the rotational motion of the urging element. As the adjustment element is actuated by the urging element, the diameter-adjusting elements are caused by the adjustment element to jut out of the through holes of the tubular body so as to bring about an increase in diameter of the tubular body. For example, the adjustment element is made up of a plurality of spherical bodies in contact with each other while the urging element is a screw. In the meantime, the open top of the tubular body is a threaded hole engageable with the screw serving as the urging element. The positions of the spherical bodies of the adjustment element are adjusted by the screw which is caused to advance in the threaded hole of the tubular body. As the spherical bodies of the adjustment element are actuated by the screw; the diameter-adjusting elements are caused to jut out of the through holes of the tubular body. The extent to which the diameter-adjusting elements are caused to jut out depends on the extent to which the screw is caused to advance in the threaded hole of the tubular body. When the eccentric bearing is used as the adjustment element, it is recommended that the urging element is columnar in shape and is made integrally with the adjustment element.

The foregoing objectives, features, functions and advantages of the present invention will be more readily understood upon a thoughtful deliberation of the following detailed description of the preferred embodiments of the present invention in conjunction with the accompanying drawings.

BRIEF DESCRIPTION OF THE DRAWINGS

FIGS. 1a–1c are schematic views of a first preferred embodiment of the present invention.

DETAILED DESCRIPTION OF THE EMBODIMENTS

As shown in FIG. 1a, a hollow tubular body 10 of the first preferred embodiment of the present invention is similar in profile to an artificial hip joint of the prior art. The tubular body 10 is provided with a threaded hole 11, a plurality of through holes 12, and a hollow interior 13.

Figure 1C:
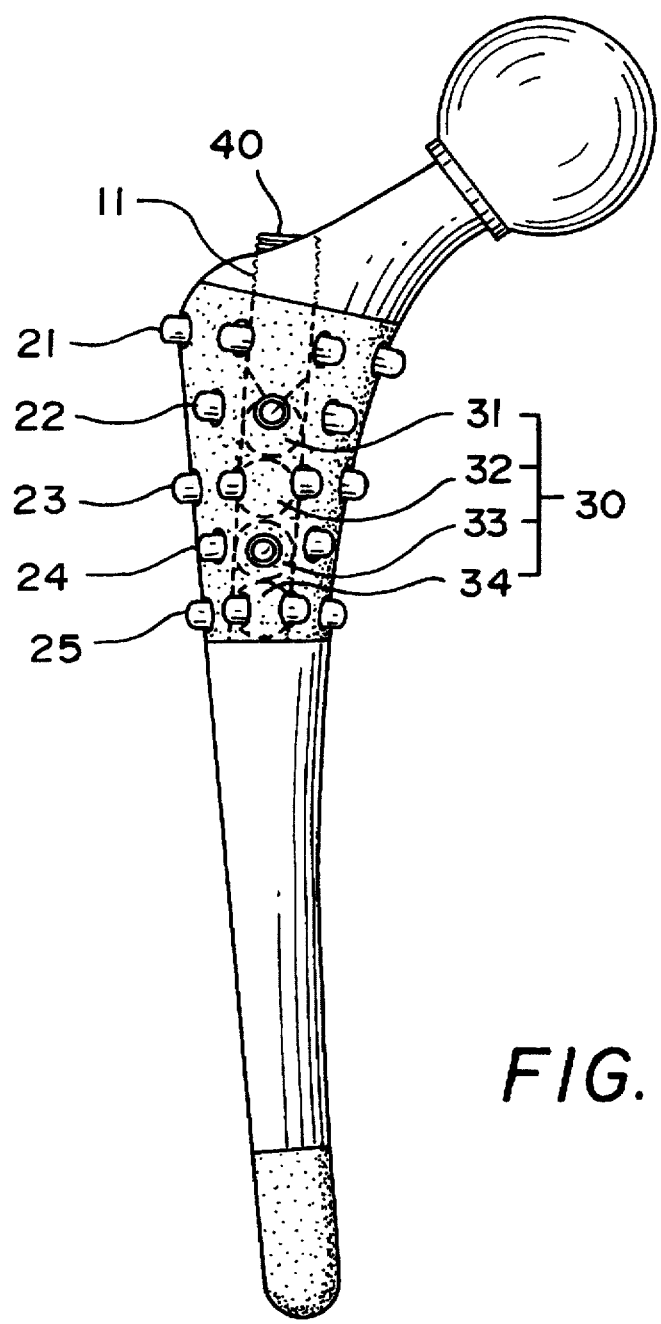
Figure 2:
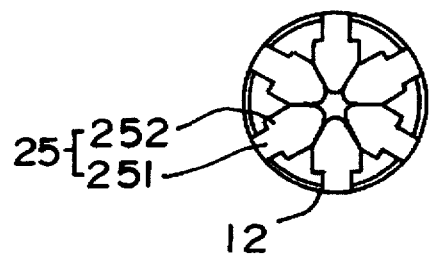
FIG. 2 shows a sectional view taken in the direction indicated by a line II—II as shown in FIG. 1b.

Now referring to FIGS. 1b, 1c and 1d, the first preferred embodiment of the present invention comprises a plurality of the diameter-adjusting elements 21–25, which are received respectively in the through holes 12 of the tubular body 10. The first preferred embodiment of the present invention further comprises an adjustment element 30 which is composed of a plurality of spherical bodies 31–34 or a corrugated shaft 30". The threaded hole 11 of the tubular body 10 is engaged with a screw 40 serving as the urging element. As shown is FIG. 1c, the screw 40 is tightened so as to actuate the adjustment element 30 to cause the diameter-adjusting elements 21–25 to jut out of the through holes 12 in order to urge intensively the bone marrow cavity of a bone intended to be fixed. As shown in FIG. 2, the diameter-adjusting element 25 is provided with a columnar body 251 capable of urging securely the bone marrow cavity of a fractured bone. In addition, the diameter-adjusting element 25 is provided with a protuberance 252 for preventing the diameter-adjusting element 25 from becoming disengaged with the through hole 12 in which the diameter-adjusting element 25 is received.

Figure 3A:
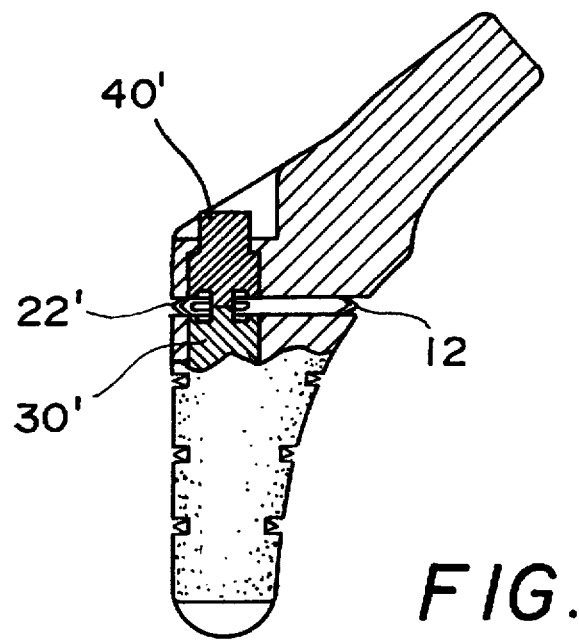
FIGS. 3a–3f are schematic views of a second preferred embodiment of the present invention.
Figure 3B:
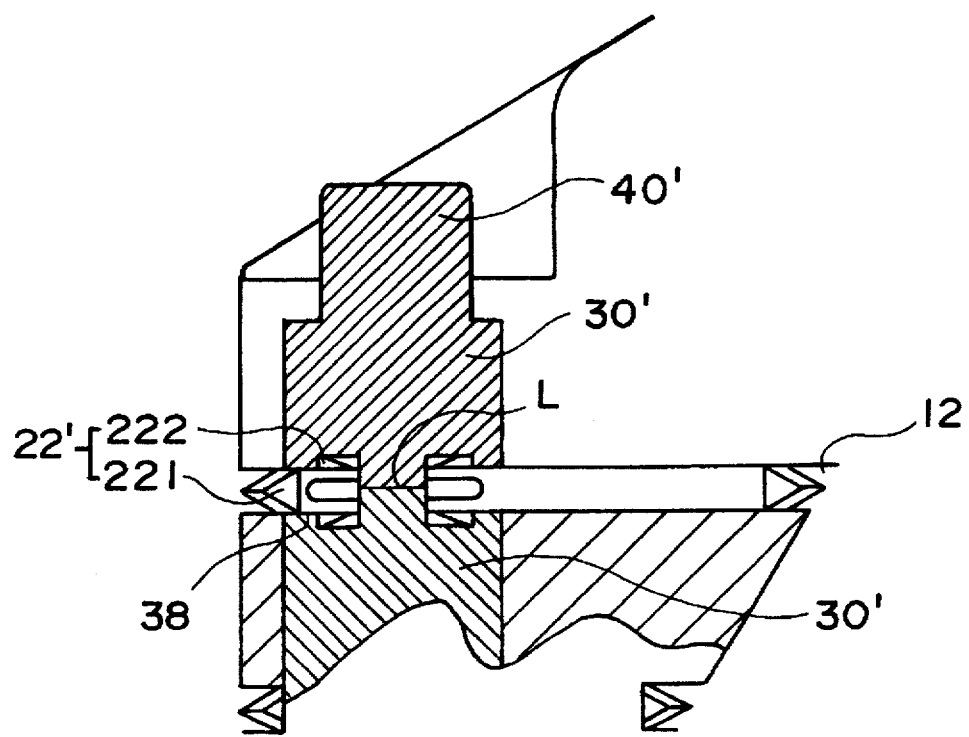

As illustrated in FIG. 3a, the second preferred embodiment of the present invention comprises an eccentric bearing 30' serving as the adjustment element. As shown in FIG. 3b, the eccentric bearing 30' is provided with a retaining means 38 engageable with a holding element 222 of the diameter-adjusting element 22' which has a tapered outer end 221.

Figure 3C:
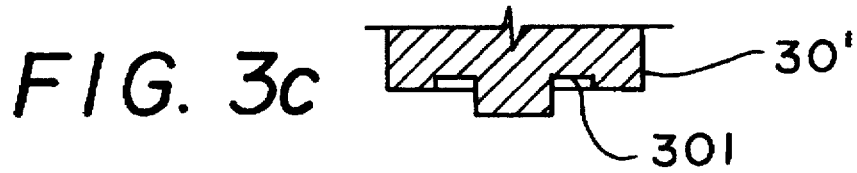
Figure 3D:
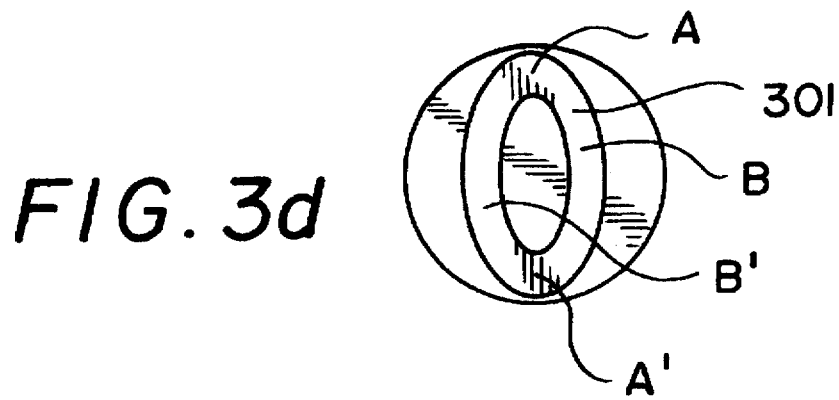
Figure 3E:
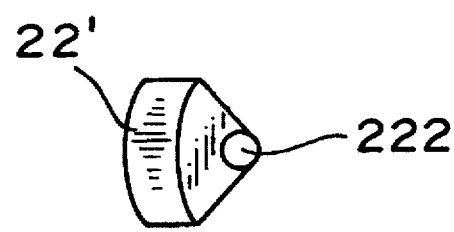
Figure 3F:
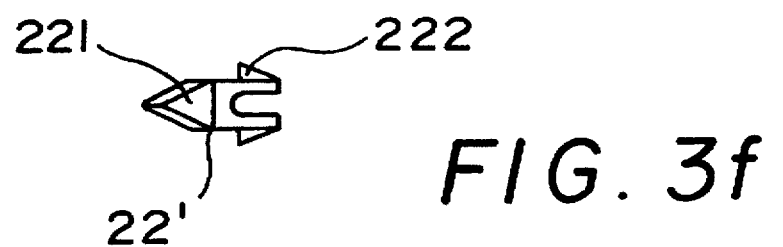

FIG. 3c is a sectional view of a portion indicated by a letter "L" as shown in FIG. 3b. The eccentric bearing 30' is provided with an oval slot 301 and is made integrally with the urging element 40' shown in FIGS. 3a and 3b. When the urging element 40' is turned to actuate the eccentric bearing 30' in such a manner that the holding element 222 of the diameter-adjusting element 22' is retained by the oval slot 301 at point B or B' as shown in FIG. 3d, and that the diameter-adjusting element 22' is caused to remain in its entirety in the through hole 12 shown in FIGS. 3a and 3b. After the fixation device of the present invention is implanted, the urging element 40' is rotated to actuate the eccentric bearing 30' such that the holding element 222 of the diameter-adjusting element 22' is retained securely by the oval slot 301 at points A and A' shown in FIG. 3d, and that the diameter-adjusting element 22' is caused to jut out of the through hole 12 to urge firmly the bone marrow cavity of a bone to be fixed. FIGS. 3e and 3f are the top view and side view of the diameter-adjusting element 22' respectively, and the definitions of the numerals of 221 and 222 are the same as in FIG. 3b.

The embodiments of the present invention described above are to be regarded in all respect as merely illustrative and not restrictive. Accordingly the present invention may be embodied in other specific forms without deviating from the spirit thereof. The present invention is therefore to be limited only by the scope of the following appended claims.

What is claimed is:

1. A bone marrow cavity fixation device for treating a fractured bone comprising:

a tubular body provided axially with a hollow interior having an open top, said tubular body further provided peripherally with a plurality of through holes in communication with said hollow interior and the outside of said tubular body;

a plurality of diameter-adjusting elements dimensioned and shaped to be received movably in said through holes of said tubular body, said diameter-adjusting elements provided respectively with a holding element capable of preventing said diameter-adjusting elements from becoming disengaged with said through holes;

an adjustment element received in said hollow interior of said tubular body such that inner ends of said diameter-adjusting elements are urged by said adjustment element wherein said adjustment element comprises a plurality of generally spherical or oval bodies in contact with one after another; and an urging element received in said hollow interior of said tubular body via said open top such that said adjustment element can be actuated by a rotational motion of said urging element so as to cause said diameter-adjusting elements to jut out of said through holes of said tubular body;

wherein a retaining means is provided engageable with said holding element of each of said diameter-adjusting elements for preventing said diameter-adjusting elements from becoming disengaged with said through holes of said tubular body.

2. The fixation device as defined in claim 1, wherein said open top of said hollow interior of said tubular body has a threaded hole; and wherein said urging element comprises a screw engageable with said threaded hole of said tubular body.

3. A bone marrow cavity fixation device for treating a fractured bone comprising:

- a tubular body provided axially with a hollow interior having an open top, said tubular body further provided peripherally with a plurality of through holes in communication with said hollow interior and the outside of said tubular body;
- a plurality of diameter-adjusting elements dimensioned and shaped to be received movably in said through holes of said tubular body, said diameter-adjusting elements provided respectively with a holding element capable of preventing said diameter-adjusting elements from becoming disengaged with said through holes;
- an adjustment element received in said hollow interior of said tubular body such that inner ends of said diameter-adjusting elements are urged by said adjustment element wherein said adjustment element comprises a rotatable member having an eccentric cam slot in contact with the diameter adjusting elements; and
- an urging element received in said hollow interior of said tubular body via said open top such that said adjustment element can be actuated by a rotational motion of said urging element so as to cause said diameter-adjusting elements to jut out of said through holes of said tubular body;
- wherein a retaining means is provided engageable with said holding element of each of said diameter-adjusting elements for preventing said diameter-adjusting elements from becoming disengaged with said through holes of said tubular body.

4. The fixation device as defined in claim 3, wherein said urging element is columnar in shape and is made integrally with said adjustment element.

* * * * *